(12) United States Patent
Lee et al.

(10) Patent No.: US 12,102,451 B2
(45) Date of Patent: Oct. 1, 2024

(54) BIOSIGNAL PROCESSING APPARATUS BASED ON INTELLIGENT CONTROL

(71) Applicants: SKAIChips Co., Ltd., Suwon-si (KR); Research & Business Foundation SUNGKYUNKWAN UNIVERSITY, Suwon-si (KR)

(72) Inventors: Kang Yoon Lee, Seoul (KR); Jong Wan Jo, Suwon-si (KR); Young Gun Pu, Suwon-si (KR); Imran Ali, Suwon-si (KR); Dong Gyu Kim, Suwon-si (KR); Joon Hong Park, Suwon-si (KR); Dong Gyun Kim, Daejeon (KR); Yun Gwan Kim, Suwon-si (KR); Jae Bin Kim, Suwon-si (KR); Dong Soo Park, Suwon-si (KR); Sung June Byun, Seoul (KR)

(73) Assignees: SKAIChips Co., Ltd., Suwon-si (KR); Research & Business Foundation SUNGSKYUNKWAN UNIVERSITY, Suwon-si (KR)

( * ) Notice: Subject to any disclaimer, the term of this patent is extended or adjusted under 35 U.S.C. 154(b) by 551 days.

(21) Appl. No.: 17/394,419

(22) Filed: Aug. 5, 2021

(65) Prior Publication Data
US 2022/0117562 A1    Apr. 21, 2022

(30) Foreign Application Priority Data
Oct. 21, 2020    (KR) .................. 10-2020-0136472

(51) Int. Cl.
*A61B 5/00*    (2006.01)
*A61B 5/30*    (2021.01)

(52) U.S. Cl.
CPC .............. *A61B 5/7225* (2013.01); *A61B 5/30* (2021.01); *A61B 5/7264* (2013.01);
(Continued)

(58) Field of Classification Search
CPC ....... A61B 5/7225; A61B 5/30; A61B 5/7264; A61B 5/7275; A61B 2560/0214;
(Continued)

(56) References Cited

U.S. PATENT DOCUMENTS

2010/0113898 A1    5/2010    Kim et al.
2018/0295535 A1*   10/2018   Kavars ...................... G06F 1/28
(Continued)

FOREIGN PATENT DOCUMENTS

KR    10-1050280 B1    7/2011
KR    10-2012-0094870 A    8/2012
(Continued)

*Primary Examiner* — Charles Cai
(74) *Attorney, Agent, or Firm* — Insight Law Group, PLLC; Seung Lee (57) ABSTRACT

The present invention relates to an integrated circuit for processing biosignals, a biosignal processing apparatus, and a biosignal processing system, and the integrated circuit includes: a digital conversion unit for converting an analog biosignal input through a biosignal input terminal into digital biodata; and an AI block for processing a plurality of biodatas converted through the digital conversion unit according to an artificial intelligence processing flow, and outputting a result data according to processing of the plurality of biodatas.

17 Claims, 5 Drawing Sheets

(52) U.S. Cl.
CPC .... *A61B 5/7275* (2013.01); *A61B 2560/0214* (2013.01); *A61B 2560/0462* (2013.01); *A61B 2562/0271* (2013.01)

(58) Field of Classification Search
CPC .... A61B 2560/0462; A61B 2562/0271; A61B 5/002; A61B 5/294; A61B 5/311; A61B 5/388; A61B 5/24; A61B 5/304; A61N 1/36103; A61N 1/36125; A61N 1/36128; A61N 1/378; G16H 50/20; G16H 50/50; H03M 1/12; H03M 1/66; H03M 13/23
See application file for complete search history.

(56) References Cited

U.S. PATENT DOCUMENTS

| | | | | |
|---|---|---|---|---|
| 2020/0064901 A1* | 2/2020 | Almers | ............... | G06K 19/07 |
| 2020/0397383 A1* | 12/2020 | Genov | ............... | A61B 5/686 |
| 2021/0271732 A1* | 9/2021 | Ge | ............... | H04Q 3/0004 |
| 2022/0003676 A1* | 1/2022 | Mazed | ............... | G01N 21/658 |
| 2022/0158497 A1* | 5/2022 | Babakhani | ............ | A61N 1/3787 |
| 2023/0034337 A1* | 2/2023 | Gorski | ............... | G06Q 50/34 |

FOREIGN PATENT DOCUMENTS

| | | |
|---|---|---|
| KR | 10-2015-0133631 A | 11/2015 |
| KR | 10-2016-0080900 A | 7/2016 |
| KR | 10-2017-0025069 A | 3/2017 |
| KR | 10-2017-0074039 A | 6/2017 |
| KR | 10-2019-0130925 A | 11/2019 |
| KR | 10-2030081 B1 | 11/2019 |
| KR | 10-2020-0070089 A | 6/2020 |

* cited by examiner

BIOSIGNAL PROCESSING APPARATUS BASED ON INTELLIGENT CONTROL

CROSS REFERENCE TO RELATED APPLICATION

The present application claims the benefit of Korean Patent application No. 10-2020-0136472 filed on Oct. 21, 2020, the entire contents of which are incorporated herein by reference.

BACKGROUND OF THE INVENTION

Field of the Invention

The present invention relates to a biosignal processing apparatus based on intelligent control, and more specifically, to a biosignal processing apparatus based on intelligent control, which can process various types of biosignals for medical/biological purposes using a built-in artificial intelligence engine by utilizing power supplied from various external power sources.

Background of the Related Art

In recent years, new viruses or new diseases are widely spread. Globally, epidemics of infectious diseases such as SARS in 2003, new influenza in 2009, and COVID-19 in 2020 pose a serious threat to mankind.

Detecting early these new diseases or new viruses (hereinafter referred to as 'new diseases') and preventing diseases transmitted by infected persons emerges as an important technical task. Diagnostic kits for early detection of new diseases or the like are known. Although the diagnostic kits process biosignals received from biosensors that respond to new diseases and determine whether or not a person is infected with a new disease, it is known that the false detection rate of the diagnostic kits is very high in the case of new diseases.

In addition, a biosensor that senses biosignals generates and outputs a signal proportional to a trace amount of biomolecular weight of blood, body fluid, or other analyte of a human body to be sensed. According to biosensor type, a specific biosensor may output a current signal proportional to a targeted biomolecular weight, and another biosensor may output a voltage signal proportional to the targeted biomolecular weight.

As integrated circuits known for processing biosignals received from the biosensors are configured to interface with only biosensors of a specific type (current signal or voltage signal), there a problem in that they may not interface with various types of biosensors.

In addition, the integrated circuits that process biosignals need to be supplied with power from the outside. The integrated circuits may be driven by DC power directly provided from the outside and perform a specified biomedical treatment. The integrated circuits that process biosignals need to be attached to or located inside a human body. In this case, an alternative method of supplying power other than the external power supply is required.

As such, it needs to provide a biosignal processing method capable of solving or improving existing known problems in a system that processes biosignals.

SUMMARY OF THE INVENTION

Therefore, the present invention has been made in view of the above problems, and it is an object of the present invention to provide an integrated circuit for processing biosignals, a biosignal processing apparatus, and a biosignal processing system, which can detect diseases from biosignals received from a human body or connect damaged nerves, and reduce the size and power consumption, while being able to be mass produced.

In addition, another object of the present invention is to provide an integrated circuit for processing biosignals, a biosignal processing apparatus, and a biosignal processing system, which can improve and reduce a false detection rate of disease by utilizing a learned and updated artificial intelligence engine and can be widely and generally used by interfacing with various types of biosensors.

In addition, another object of the present invention is to provide an integrated circuit for processing biosignals, a biosignal processing apparatus, and a biosignal processing system, which can harvest power needed inside the integrated circuit from various types of external signals, and provide the power to the integrated circuit that processes the biosignals, while being able to be used in various biosignal processing environments.

The technical problems to be solved in the present invention are not limited to the technical problems mentioned above, and unmentioned other technical problems will be clearly understood by those skilled in the art from the following descriptions.

To accomplish the above objects, according to one aspect of the present invention, there is provided an integrated circuit for processing biosignals, the integrated circuit comprising: a digital conversion unit for converting an analog biosignal input through a biosignal input terminal into a digital biodata; and an AI block for processing a plurality of biodata converted through the digital conversion unit according to an artificial intelligence processing flow, and outputting a result data according to processing of the plurality of biodata.

In the integrated circuit for processing biosignals described above, the digital conversion unit includes: a demultiplexer for outputting the analog biosignal output from the biosignal input terminal to a first output line or a second output line according to a type signal that is input through a type input terminal; a trans-impedance amplifier for amplifying the analog biosignal of the first output line and outputting the amplified biosignal; a low-noise amplifier for amplifying the analog biosignal of the second output line and outputting the amplified biosignal; and a first multiplexer for outputting a biosignal selected from the biosignal of the trans-impedance amplifier and the biosignal of the low-noise amplifier according to the type signal.

In the integrated circuit for processing biosignals described above, the digital conversion unit further includes: a temperature sensor; a second multiplexer for outputting the biosignal output from the first multiplexer or a temperature signal output from the temperature sensor according to a selection signal received from the AI block; and an ADC for converting an analog signal output from the second multiplexer into a digital data.

In the integrated circuit for processing biosignals described above, the digital conversion unit includes the demultiplexer, the trans-impedance amplifier, the low-noise amplifier, the first multiplexer, the second multiplexer, and the ADC in plurality to independently convert analog biosignals input through a plurality of biosignal input terminals into a plurality of digital biodata, and output the digital biodata to the AI block.

The integrated circuit for processing biosignals described above further comprises a power supply unit for supplying power to the digital conversion unit and the AI block from a supplied main power or a signal recognized from the outside, wherein the power supply unit outputs power generated from the signal recognized from the outside to the digital conversion unit and the AI block as a voltage of a specified level according to whether the main power is detected.

In the integrated circuit for processing biosignals described above, the power supply unit includes: a main power detector for detecting the main power from a main power input terminal, and outputting a detection signal indicating whether or not the main power is detected; a harvester for generating power from a signal recognized from the outside of the integrated circuit for processing biosignals; and a third multiplexer for selecting and outputting one among the power from the harvester and the main power of the main power input terminal according to the detection signal of the main power detector, wherein the power output from the third multiplexer is supplied to the digital conversion unit and the AI block.

In the integrated circuit for processing biosignals described above, the harvester includes: a solar energy harvester for harvesting power from a solar signal output from a solar input terminal; an RF harvester for harvesting power from an RF signal output from an RF input terminal; a vibration/electrostatic harvester for harvesting power from a vibration/electrostatic signal output from a vibration/static-electricity input terminal; and a buck-boost converter for increasing or decreasing power received from one or more among the solar energy harvester, the RF harvester, and the vibration/electrostatic harvester, and outputting the increased or decreased power to the third multiplexer.

In the integrated circuit for processing biosignals described above, the solar energy harvester includes a Maximum Power Point Tracker (MPPT), the RF harvester includes a reconfigurable RF-DC converter, and the vibration/electrostatic harvester includes a rectifier, wherein the harvesting power output through the buck-boost converter is stored through a capacitor outside the integrated circuit for processing biosignals.

In the integrated circuit for processing biosignals described above, the AI block predicts infection of a disease from the biodata and outputs a predicted result, or predicts an output signal of a neural network of a human body from the biodata and outputs the predicted signal.

In addition, a biosignal processing apparatus according to an aspect of the present invention comprises: a digital conversion unit for converting an analog biosignal into a digital biodata; and an AI block for processing a plurality of biodata converted through the digital conversion unit according to an artificial intelligence processing flow and outputting a result data according to processing of the plurality of biodata using an analog PIM.

In the biosignal processing apparatus described above, the AI block includes: a memory for storing a plurality of biodata received from the digital conversion unit; the analog PIM capable of storing a plurality of analog data of each of a plurality of kernels, updating the plurality of analog data of the plurality of kernels, and outputting a plurality of digital data corresponding to the plurality of kernels; and an AI digital controller for generating a predicted result data by applying a processing flow of an artificial intelligence algorithm using a plurality of corresponding digital data of the plurality of kernels received from the analog PIM, and the plurality of biodata of the memory.

In the biosignal processing apparatus described above, the AI digital controller applying a CNN algorithm generates a plurality of feature maps by a convolution operation between the plurality of biodata of the memory and the plurality of corresponding digital data of the plurality of kernels of the analog PIM, and stores the feature maps in a memory in a first convolution operation process, and generates a plurality of digital data of a plurality of kernels to be used in a second convolution operation process subsequent to the first convolution operation process, and stores a plurality of digital data of each of a plurality of kernels to be updated in the analog PIM.

In the biosignal processing apparatus described above, the analog PIM includes: M DACs; an SRAM array including L of M SRAMs respectively connected the M DACs according to the number of the plurality of kernels, each SRAM storing analog data received from a connected DAC; and L or more ADCs connected to the SRAMs of the SRAM array to convert an analog data of the SRAM into a digital data of a specified number of bits, wherein M and L are equal to or greater than 2.

In the biosignal processing apparatus described above, the biosignal processing apparatus is an integrated circuit for processing biosignals.

In addition, a biosignal processing system according to an aspect of the present invention comprises the integrated circuit for processing biosignals described above.

The biosignal processing system described above further comprises: a capacitor for storing harvesting power; and a biosensor for generating an analog biosignal using power harvested by the integrated circuit for processing biosignals, and outputting the generated analog biosignal of current or voltage to a biosignal input terminal of the integrated circuit for processing biosignals, wherein the integrated circuit for processing biosignals including a digital conversion unit and an AI block further includes a harvester for generating harvesting power that can be used by the biosensor.

The biosignal processing system described above further comprises: an RF matching network capable of matching an RF signal of a first ISM band or a second ISM band; and a limiter for limiting a vibration/electrostatic signal according to vibration/static electricity, wherein the harvester of the integrated circuit for processing biosignals includes: an RF harvester for harvesting power from the RF signal output from an RF input terminal; a vibration/electrostatic harvester for harvesting power from the vibration/electrostatic signal output from a vibration/static-electricity input terminal; a buck-boost converter for increasing or decreasing power received from one or more among the RF harvester and the vibration/electrostatic harvester, and outputting the increased or decreased power as harvesting power; and a harvester controller for controlling generation of harvesting power from an external signal by controlling the RF harvester and the vibration/electrostatic harvester.

In the biosignal processing system described above, the harvester controller outputs a control signal for matching to the first ISM band to the RF matching network through an output terminal, measures a first RF power generated by the RF harvester, and then outputs a control signal for matching to the second ISM band to the RF matching network through the output terminal, measures a second RF power generated by the RF harvester, and then outputs a control signal for controlling the RF matching network based on a measurement signal of the first RF power and a measurement signal of the second RF power, and reconfigures the RF harvester.

The biosignal processing system described above further comprises an RF module for transmitting a radio signal, wherein an AI block of the integrated circuit for processing biosignals predicts a signal output through a neural network of a human body from a biosignal received from a nerve cell of the human body, and transmits a data indicating the predicted signal through the RF module.

In the biosignal processing system described above, the biosignal processing system is a diagnostic kit that predicts infection of a disease from blood or body fluid or a medical device that can replace a signal of a neural network of a human body, using a learned artificial intelligence technique.

DESCRIPTION OF SYMBOLS

| | |
|---|---|
| 10: Biosignal processing apparatus | |
| 100: Digital conversion unit | |
| 110: Demultiplexer | 120: Trans-impedance amplifier |
| 130: Low-noise amplifier | 140: First multiplexer |
| 150: PGA | 160: Temperature sensor |
| 170: Second multiplexer | 180: ADC |
| 300: Power supply unit | 310: Main power detector |
| 320: Harvester | 321: Solar energy harvester |
| 323: RF harvester | |
| 325: Vibration/Electrostatic harvester | |
| 327: Buck-boost converter | 329: Harvester controller |
| 330: Third multiplexer | |
| 340: First LDO | 350: Second LDO |
| 360: Third LDO | 500: AI block |
| 510: AI digital controller | 530: Memory |
| 550: Analog PIM | |
| 551: Main controller | 552: DAC controller |
| 553: DAC | |
| 554: SRAM array | 554-1: SRAM |
| 555: SRAM array controller | 556: ADC controller |
| 557: ADC | |
| 700: Output terminal | 900: Input terminal |
| 20: Biosensor | 30: Solar cell |
| 40: RF matching network | 50: Limiter |
| 60: Input module | 70: Output module |
| 80: RF module | 90: Capacitor |

DETAILED DESCRIPTION OF THE PREFERRED EMBODIMENT

The objects, features and advantages described above will become further clear through the detailed description described below in detail with reference to the accompanying drawings, and accordingly, those skilled in the art may easily embody the technical spirit of the present invention. In addition, when it is determined in describing the present invention that a detailed description of a known technique related to the present invention may unnecessarily obscure the gist of the present invention, the detailed description will be omitted. Hereinafter, preferred embodiments according to the present invention will be described in detail with reference to the accompanying drawings.

Figure 1:
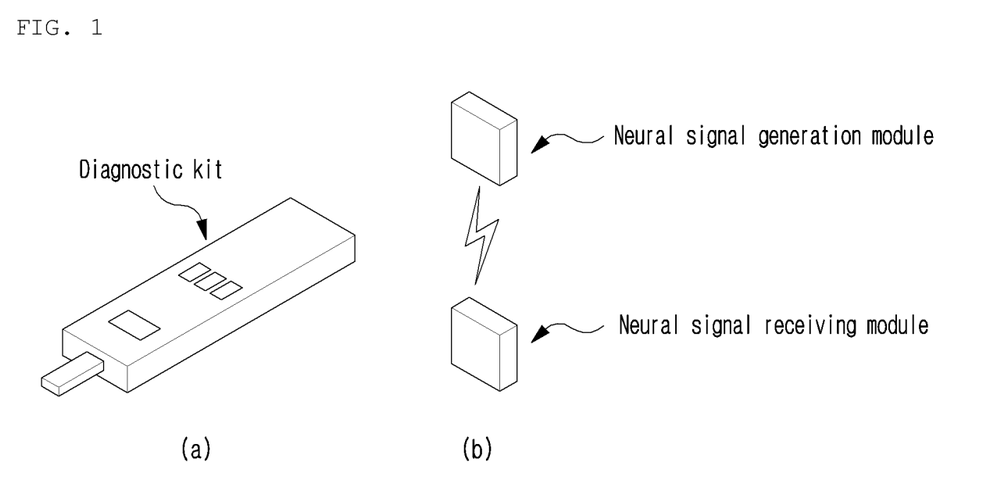
FIG. 1 is a view showing an implementation example of a biosignal processing system implemented according to the present invention.

FIG. 1 is a view showing an implementation example of a biosignal processing system implemented according to the present invention.

The biosignal processing system implemented according to the present invention may be applied to biological or medical fields, and implemented as a diagnostic kit ((a) in FIG. 1) or a medical device ((b) in FIG. 1).

The biosignal processing system according to the present invention may be implemented as a diagnostic kit that can predict infection of a disease from body fluid, blood or saliva using a learned artificial intelligence technique, or may be implemented as a medical device that can replace a (broken) neural signal of the neural network of a human body.

The diagnostic kit may predict infection of a disease by applying artificial intelligence technology to biosignals of body fluid, blood and saliva, and output a predicted result through a buzzer, an LED or the like. The medical device includes a neural signal generation module and a neural signal receiving module, and the neural signal generation module is located at one end (e.g., spine, head, etc.) inside a human body where the neural network is broken, and may predict an output signal from the biosignal of the neural signal received from the brain, the spinal cord or the like in the human body to the other end (e.g., leg, foot, finger, etc.) inside the human body by applying artificial intelligence technology, and transmit a data indicating the predicted neural signal to the neural signal receiving module through an RF signal. The neural signal receiving module located at the other end of the human body where the neural network is broken may receive the predicted signal through an RF module, generate a neural signal corresponding to the predicted signal, and output the neural signal to the nerve cell of the broken neural network.

Although the biosignal processing system according to the present invention is described based on an example of a diagnostic kit and a medical device, it may be utilized in various biological or medical fields and applications.

Figure 2:
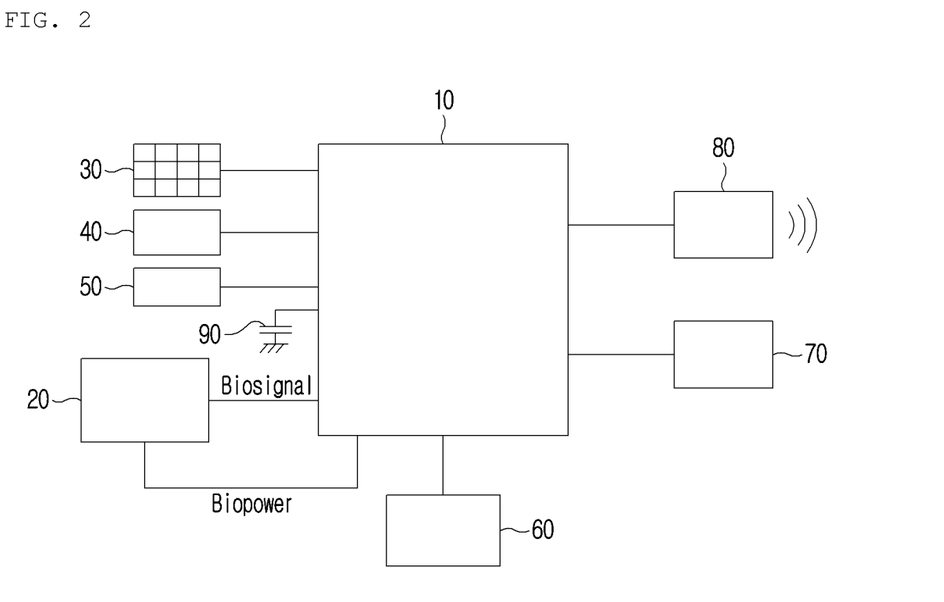
FIG. 2 is an exemplary block diagram showing a biosignal processing system.

FIG. 2 is an exemplary block diagram showing a biosignal processing system.

According to FIG. 2, the biosignal processing system includes a biosignal processing apparatus 10, and may further include a biosensor 20, a solar cell 30, an RF matching network 40, a limiter 50, an input module 60, an output module 70, an RF module 80, and a capacitor 90.

According to design examples, the biosignal processing system may have various block configurations. For example, the diagnostic kit may be configured by omitting one or more blocks among the RF module 80, the solar cell 30, the RF matching network 40, the limiter 50, and the capacitor 90. The neural signal generation module may be configured by omitting the input module 60 and/or the output module 70.

Describing the biosignal processing system with reference to FIG. 2, the biosignal processing apparatus 10 processes biosignals received from a human body and outputs a processing result. For example, the biosignal processing apparatus 10 may predict infection of a disease from blood, saliva, secretions, or the like of the human body and output a prediction result. Alternatively, the biosignal processing apparatus 10 may predict a neural signal to be transmitted to the neural signal receiving module from a nerve cell signal of the neural network of the human body and output a prediction result through an RF signal.

The biosignal processing apparatus 10 may be implemented in various forms. Preferably, the biosignal processing apparatus 10 may be implemented as an integrated circuit for processing biosignals. The biosignal processing apparatus 10 may be implemented as a system semiconductor of an IC, chipset, or wafer form and embedded in the diagnostic kit or the neural signal generation module.

The biosignal processing apparatus 10, which is an integrated circuit for processing biosignals, includes various input terminals 900 and output terminals 700 and interfaces with other blocks through the input terminal 900 and the output terminal 700 to configure the biosignal processing system.

The biosignal processing apparatus 10 will be described below in detail with reference to FIG. 3.

The biosensor 20 senses biosignals and outputs the sensed biosignals to the biosignal processing apparatus 10 (an integrated circuit for processing biosignals). The biosensor 20 may sense a biosignal from the blood, saliva, secretions, or the like or from a nerve cell of the neural network of a human body, and output the sensed biosignal as an analog biosignal of current or voltage.

The biosensor 20 may output an analog biosignal having a current proportional to the amount of biosignal of a detection target or an analog biosignal having a voltage proportional to the amount of biosignal of a detection target. The biosensor 20 may be classified into a voltage output type or a current output type according to the type of a detection target. The biosignal processing apparatus 10 according to the present invention is preferably configured to process biosignals by commonly interfacing with both the current output type and the voltage output type, regardless of the type of the biosensor 20.

The biosensor 20 may output biosignals using biopower supplied from the biosignal processing apparatus 10. The biopower may be power harvested by the biosignal processing apparatus 10 (an integrated circuit for processing biosignals) through the solar cell 30, the RF matching network 40, and/or the limiter 50.

The solar cell 30 converts solar energy into electrical energy. The solar cell 30 is made of a material such as silicon or the like, converts light energy radiated from the sun into electrical energy, and outputs the electrical energy to the biosignal processing apparatus 10.

The RF matching network 40 matches an RF signal of a specific frequency band among a plurality of frequency bands that can be matched. The RF matching network 40 is configured to match RF signals of several Industrial Scientific Medical (ISM) bands. For example, the RF matching network 40 may be configured to match an RF signal of a band among a 2.4 GHz band and a 5.8 GHz band.

The RF matching network 40 includes a circuit (e.g., an RLC circuit) for matching an RF signal of 2.4 GHz band outside the biosignal processing system and a circuit for matching an RF signal of 5.8 GHz band outside the biosignal processing system, senses an RF signal through setting of a circuit for matching one ISM band among the two ISM bands according to a control signal received from the biosignal processing apparatus 10, and outputs the sensed RF signal (corresponding an electrical signal) to the biosignal processing apparatus 10.

An arbitrary RF signal existing outside the biosignal processing system may be sensed through the RF matching network 40, and the biosignal processing system may generate harvesting power from the sensed RF signal.

The limiter 50 limits a vibration and/or electrostatic signal sensed according to vibration and/or static electricity. For example, the limiter 50 may be configured to output a vibration/electrostatic signal lower than a set voltage level to the biosignal processing apparatus 10. Through the limiter 50, the biosignal processing system may generate harvesting power from vibration or static electricity outside the biosignal processing system.

The input module 60 receives a user input of the biosignal processing system. The input module 60 includes buttons, touchpads, switches, and the like, and may provide the biosignal processing apparatus 10 with various inputs such as power on/off of the biosignal processing system, a biosignal process request, and the like.

The output module 70 outputs various signals. The output module 70 includes LEDs, buzzers, speakers, and the like, and may output visual and/or auditory signals indicating a processing result generated by the biosignal processing apparatus 10.

The RF module 80 transmits a radio signal. The RF module 80 may transmit a radio signal (RF signal) of 2.4 GHz, 5.8 GHz, or 900 MHz band. The neural signal generation module of the biosignal processing system transmits a radio signal according to a promised communication protocol through the RF module 80, and the neural signal receiving module may receive the radio signal and generate a neural signal of a predicted signal corresponding to the radio signal, and output the generated neural signal to the broken neural network (nerve cell) of a human body.

The capacitor 90 stores power. The capacitor 90 may store harvesting power harvested (generated) through various signals sensed in an external environment of the biosignal processing apparatus 10. The capacitor 90 is connected to the output terminal 700 of the biosignal processing apparatus 10 (integrated circuit for processing biosignals) that outputs harvesting power, and stores the harvesting power output from the harvesting power output terminal 700.

Figure 3:
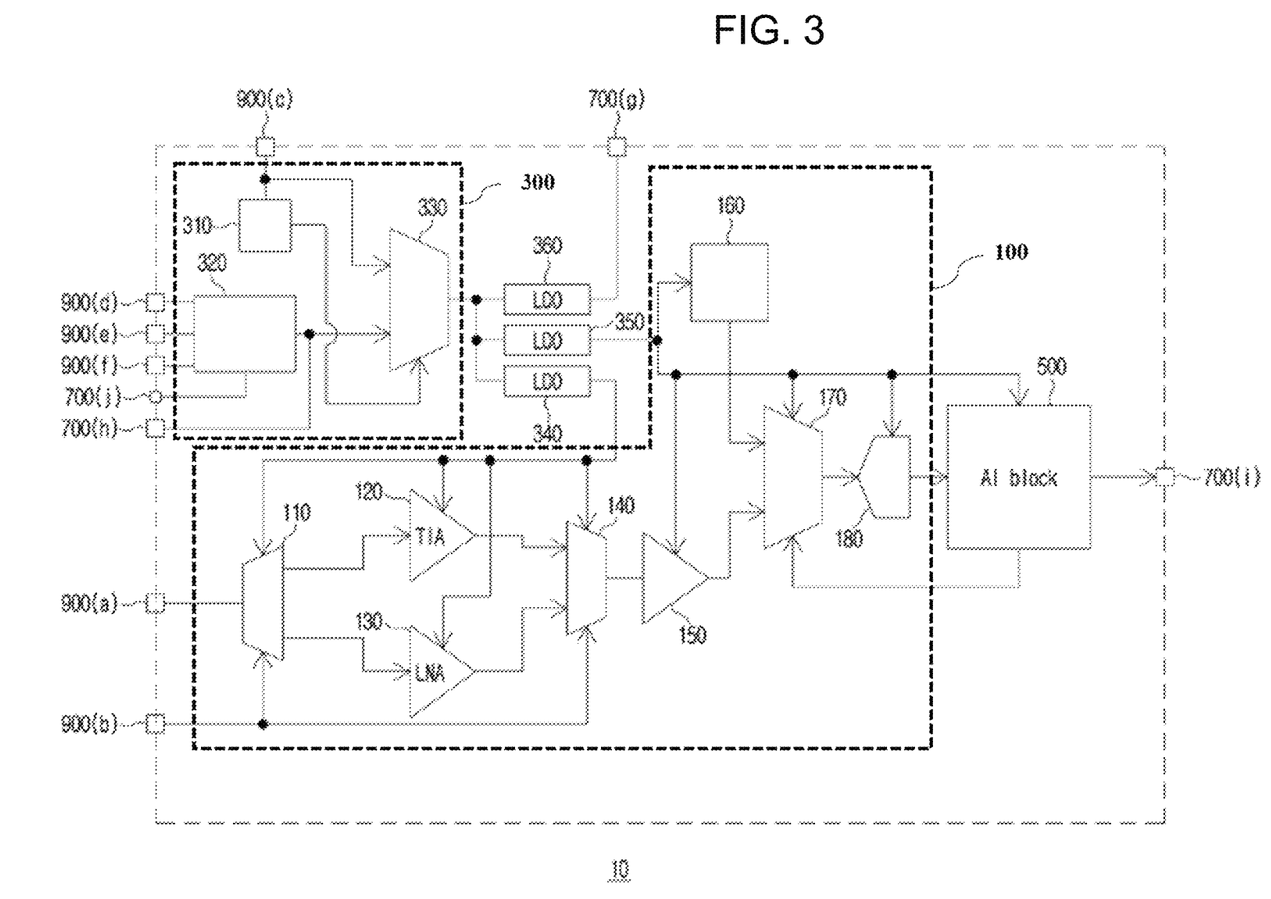
FIG. 3 is an exemplary block diagram showing a biosignal processing apparatus.

FIG. 3 is an exemplary block diagram showing a biosignal processing apparatus 10.

The block diagram of FIG. 3 shows an example of the biosignal processing apparatus 10 configured as an integrated circuit for processing biosignals. According to FIG. 3, the biosignal processing apparatus 10, which is an integrated circuit for processing biosignals, is configured to include a digital conversion unit 100, a power supply unit 300, an AI block 500, a plurality of input terminals 900 and a plurality of output terminals 700 for interfacing with other external blocks (see FIG. 2). When the biosignal processing apparatus 10 is not an integrated circuit for processing biosignals, the biosignal processing apparatus 10 may be configured by omitting the input terminals 900 and/or the output terminals 700.

The input terminal 900 receives a signal from the outside of the biosignal processing apparatus 10. The input terminal 900 may indicate or include a pin, a pad, a port, or the like configured in the integrated circuit for processing biosignals to receive or sense a signal from a block, a circuit or the like outside the biosignal processing apparatus 10.

The biosignal processing apparatus 10 includes at least a biosignal input terminal 900 (see (a) in FIG. 3), a type input terminal 900 (see (b) in FIG. 3), a main power input terminal 900 (see (c) in FIG. 3), a solar input terminal 900 (see (d) in FIG. 3), an RF input terminal 900 (see (e) in FIG. 3), and a vibration/static-electricity input terminal 900 (see (f) in FIG. 3), and further includes other input terminals 900. For example, the biosignal processing apparatus 10 may further include an input terminal 900 for receiving clock signals from a crystal, an oscillator, or the like.

The biosignal input terminal 900 is connected to the biosensor 20 and receives biosignals from the biosensor 20. The biosignal input terminal 900 receives analog biosignals from the biosensor 20. The biosignal input terminal 900 may commonly receive analog biosignals of current type or analog biosignals of voltage type through a single input terminal. The biosensor 20 may output analog biosignals of variable current strength or analog biosignals of variable voltage strength (magnitude) according to the manufacturer or type of the sensor, and the biosignal input terminal 900 is configured to receive analog biosignals through the single input terminal 900 regardless of the output type of the biosensor 20.

The biosignal processing apparatus 10 may include a plurality of biosignal input terminals 900. For example, a biosignal processing apparatus 10 that simultaneously processes N*N (N is greater than or equal to 2, for example, N is 8, 16, or 32) sampled biosignals and outputs a processing result according to an artificial intelligence algorithm may include N biosignal input terminals 900, N*N biosignal input terminals 900, or N*M (M is greater than or equal to 2 and smaller than N) biosignal input terminals 900. The biosensor 20 is connected to a plurality of biosignal input terminals 900 and may output analog biosignals sensed to the plurality of biosignal input terminals 900.

The type input terminal 900 receives a type signal indicating an output type of the biosensor 20 connected through the biosignal input terminal 900. The type input terminal 900 receives a type signal indicating current type or voltage type. The type input terminal 900 may receive a type signal indicating, for example, logic 1 (current type or voltage type) or logic 0 (a type opposite to that of logic 1).

The main power input terminal 900 receives external power to be used by the biosignal processing apparatus 10. The main power input terminal 900 receives power from a battery or a DC power circuit provided in the biosignal processing system.

The solar input terminal 900 receives a solar signal converted from solar energy into electrical energy through the solar cell 30. The RF input terminal 900 receives an RF signal from the RF matching network 40. The vibration/static-electricity input terminal 900 is connected to the limiter 50 and receives a vibration/electrostatic signal of a voltage lower than a set voltage from the limiter 50.

Here, a specific input terminal 900 is an input/output terminal that may also be used as the output terminal 700.

The output terminal 700 outputs signals to the outside of the biosignal processing apparatus 10. The output terminal 700 may indicate or include a pin, a pad, a port, or the like configured in the integrated circuit for processing biosignals to output a generated signal to a block, a circuit or the like outside the biosignal processing apparatus 10.

The biosignal processing apparatus 10 includes at least a result data output terminal 700 (see (i) in FIG. 3), a biopower output terminal 700 (see (g) in FIG. 3), a harvesting power output terminal 700 (see (h) in FIG. 3), and a matching network control output terminal 700 (see (j) in FIG. 3).

The result data output terminal 700 outputs a result of processing biodata of an input biosignal by the AI block 500. For example, the result data output terminal 700 may predict infection of one or more diseases on the basis of biosignals generated from input blood, body fluid, or human secretions using artificial intelligence technology, and output a data indicating whether or not one or more diseases are infected or a probability of being infected. Alternatively, the result data output terminal 700 may predict an output signal from a biosignal (neural signal) of a nerve cell connected to the human body by applying artificial intelligence technology, and output a predicted signal data. The biosignal processing apparatus 10 may include one or a plurality of result data output terminals 700, and output analog or digital signals (e.g., 8-bit, 16-bit, or 32-bit data).

The biopower output terminal 700 outputs power that may be used by the biosensor 20. The biosignal processing apparatus 10 may include one or a plurality of (e.g., 4, 32, 32*4, or the like) biopower output terminals 700. The biopower output terminal 700 is connected to the biosensor 20, and outputs power (DC or AC power) used by the biosensor 20.

The harvesting power output terminal 700 outputs power harvested by the biosignal processing apparatus 10. The harvesting power output terminal 700 is connected to a harvester 320 of the power supply unit 300, and outputs harvesting power received from the harvester 320 to the outside of the integrated circuit for processing biosignals. The harvesting power output terminal 700 may be connected to the capacitor 90 outside the integrated circuit for processing biosignals, and charge the capacitor 90 through the harvesting power output from the harvester 320.

The matching network control output terminal 700 outputs a control signal to the RF matching network 40. The matching network control output terminal 700 is connected to the harvester 320 and outputs a control signal for matching to a specific ISM band (e.g., 2.4 GHz band or 5.8 GHz band) received from the harvester 320 to the RF matching network 40. For example, the matching network control output terminal 700 may output a logic signal (e.g., '1') for connecting, opening, or setting capacitors, resistors and the like for tuning impedance to the 2.4 GHz band of the RF matching network 40 or output a logic signal (e.g., '0') for connecting, opening, or setting capacitors, resistors and the like for tuning impedance to the 5.8 GHz band of the RF matching network 40.

Here, a specific output terminal 700 is an input/output terminal that may also be used as an input terminal 900. For example, the harvesting power output terminal 700 may be an input/output terminal that can store the power harvested by the harvester 320 in the capacitor 90, and supply the stored power to the digital conversion unit 100, the AI block 500, and the like of the integrated circuit for processing biosignals.

In this way, the biosignal processing apparatus 10 may include a plurality of input terminals 900, output terminals 700, and input/output terminals, and interface with blocks outside the integrated circuit for processing biosignals.

Describing the internal blocks of the biosignal processing apparatus 10 (an integrated circuit for processing biosignals), the digital conversion unit 100 converts an analog biosignal into a digital biodata. The digital conversion unit 100 converts analog biosignals input through one or a plurality of biosignal input terminals 900 into digital biodata, respectively, and outputs the converted biodata to the AI block 500.

The digital conversion unit 100 is configured to include a demultiplexer 110, a trans-impedance amplifier 120, a low-noise amplifier 130, a first multiplexer 140, a PGA 150, a temperature sensor 160, a second multiplexer 170, and an ADC 180. According to design examples, the digital conversion unit 100 may be configured to omit the PGA 150, the temperature sensor 160, and the second multiplexer 170.

The demultiplexer 110 outputs the analog biosignal output from the biosignal input terminal 900 to one output line among two output lines according to a type signal of the type input terminal 900 for selecting an output line. For example, when the type signal of the type input terminal 900 indicates current type, the demultiplexer 110 outputs an input analog biosignal to an output line connected to the trans-impedance amplifier 120 among the two output lines, and when the type signal indicates voltage type, the demultiplexer 110 outputs an input analog biosignal to an output line connected to the low-noise amplifier 130 among the two output lines.

The trans-impedance amplifier (TIA) 120 amplifies the analog biosignal of one output line of the demultiplexer 110, and outputs the amplified biosignal. The trans-impedance amplifier 120 converts and amplifies a current signal into a voltage signal, and outputs an analog biosignal of the amplified voltage signal.

The low-noise amplifier (LNA) 130 amplifies the analog biosignal of another output line of the demultiplexer 110, and outputs the amplified biosignal. The low-noise amplifier 130 amplifies an input voltage signal, and outputs an analog biosignal of the amplified voltage signal.

The first multiplexer 140 is connected to the trans-impedance amplifier 120 and the low-noise amplifier 130, and selects one biosignal among the biosignal of the trans-impedance amplifier 120 and the biosignal of the low-noise amplifier 130 according to a type signal of the type input terminal 900, and outputs the selected biosignal.

When the type signal of the type input terminal 900 indicates current type, the first multiplexer 140 selects the biosignal output from the trans-impedance amplifier 120 among the two input lines, and outputs the selected biosignal to the PGA 150. When the type signal indicates voltage type, the first multiplexer 140 selects the biosignal output from the low-noise amplifier 130, and outputs the selected biosignal.

The Programmable Gain Amplifier (PGA) 150 is connected to the first multiplexer 140 and re-amplifies the biosignal output from the first multiplexer 140. The PGA 150 amplifies and outputs a biosignal input as a gain under the control of the AI block 500 or internal setting.

As described above, with the configuration of the demultiplexer 110, the trans-impedance amplifier 120, the low-noise amplifier 130, the first multiplexer 140, and the PGA 150, the biosignal processing apparatus 10 is configured to receive both current and voltage inputs according to an output type of the biosensor 20, and performs an amplification operation needed according thereto.

The temperature sensor 160 senses the temperature of the biosignal processing apparatus 10. The temperature sensor 160 outputs an analog temperature signal corresponding to the sensed temperature.

The second multiplexer 170 is connected to (the PGA 150 of) the first multiplexer 140 and the temperature sensor 160 and outputs the biosignal of the first multiplexer 140 or the temperature signal received from the temperature sensor 160 according to a selection signal received from the AI block 500. For example, the second multiplexer 170 outputs the biosignal of the first multiplexer 140 output through the PGA 150 according to the selection signal of logic 0 received from the AI block 500 and outputs the temperature signal of the temperature sensor 160 according to the selection signal of logic 1.

The Analog Digital Converter (ADC) 180 is connected to the second multiplexer 170 and converts an analog signal output from the second multiplexer 170 into a digital signal. The ADC 180 may convert the analog temperature or the analog biosignal received from the second multiplexer 170 into digital data of a specified number of bits (e.g., 8 bits, 12 bits, 16 bits, 32 bits, or the like), and output the digital data.

Here, the digital conversion unit 100 of the biosignal processing apparatus 10 may be configured to include a plurality of demultiplexers 110, trans-impedance amplifiers 120, low-noise amplifiers 130, first multiplexers 140, PGAs 150, second multiplexers 170, and ADCs 180.

For example, a biosignal processing apparatus 10 that simultaneously samples and processes N*N (N is greater than or equal to 2, for example, N is 8, 16, or 32) biosignals using artificial intelligence may include N biosignal input terminals 900, N demultiplexers 110, N trans-impedance amplifiers 120, N low-noise amplifiers 130, N first multiplexers 140, N PGAs 150, N second multiplexers 170, and N ADCs 180.

A biosignal input terminal 900, a demultiplexer 110, a trans-impedance amplifier 120, a low-noise amplifier 130, a first multiplexer 140, a PGA 150, a second multiplexer 170, and ADC 180 connected to each other convert a single analog biosignal into a digital biodata and output the digital biodata to the AI block 500. Another biosignal input terminals 900, another demultiplexer 110, another trans-impedance amplifier 120, another low-noise amplifier 130, another first multiplexer 140, another PGA 150, another second multiplexer 170, and another ADC 180 connected to each other converts another single analog biosignal into a digital biodata and outputs the digital biodata to the AI block 500.

In this way, (the digital conversion unit 100 of) the biosignal processing apparatus 10 may include a plurality of demultiplexers 110, trans-impedance amplifiers 120, low-noise amplifiers 130, first multiplexers 140, PGAs 150, second multiplexers 170, and ADCs 180, and independently convert a plurality of analog biosignals input through a plurality of biosignal input terminals 900 into a plurality of digital biodata, and output the digital biodata to the AI block 500.

The digital conversion unit 100 of the biosignal processing apparatus 10 may have various modifications according to hardware design examples.

The power supply unit 300 supplies power needed for driving or operation to the AI block 500, the digital conversion unit 100, and even the external biosensor 20. The power supply unit 300 may convert main power provided directly from the outside of the biosignal processing apparatus 10 (integrated circuit for processing biosignals), and supply the converted DC power to the digital conversion unit 100, the AI block 500, and the like. Alternatively, the power supply unit 300 harvests power from a signal recognized from the outside of the biosignal processing apparatus 10 (integrated circuit for processing biosignals), and outputs the harvesting power so as to be stored or supplies the harvesting power to the digital conversion unit 100, the AI block 500, and the like.

The power supply unit 300 is configured to output the power generated from an external recognition signal to the digital conversion unit 100 and the AI block 500 as power of a specified level according to whether the main power output from the main power input terminal 900 is detected.

When the main power output from the main power input terminal 900 is detected, the power supply unit 300 outputs, from the main power, DC power (e.g., 0.7V, 1.2V, 3.3V, or the like) to be supplied to the digital conversion unit 100 and the AI block 500 inside the biosignal processing apparatus 10 (integrated circuit for processing biosignals) and the external biosensor 20. In addition, while the main power is supplied to the internal blocks, the power supply unit 300 may store the power harvested from the solar signal, the RF signal, or the vibration/electrostatic signal in the capacitor 90.

When the main power is not detected from the main power input terminal 900, the power supply unit 300 outputs the DC power (e.g., 0.7V, 1.2V, 3.3V, or the like) of the harvesting power harvested from the solar signal of solar energy, the RF signal, or the vibration/electrostatic signal to the digital conversion unit 100 and the AI block 500 inside the biosignal processing apparatus 10 and the external biosensor 20.

The power supply unit 300 includes a main power detector 310, a harvester 320, a third multiplexer 330, and one or more LDOs 340, 350, and 360.

The main power detector 310 of the power supply unit 300 detects main power output from the main power input terminal 900 of the integrated circuit for processing biosignals, and outputs a main power detection signal indicating whether or not the main power is detected.

The main power detector 310 outputs a detection signal (e.g., a signal of logic 1) indicating detection of the main power when the voltage level of the main power input terminal 900 is higher than or equal to an internally set reference level, and outputs a detection signal (e.g., a signal of logic 0) indicating non-detection of the main power when the voltage level of the main power input terminal 900 is lower than the reference level. The main power detector 310 may include a comparator or the like therein to detect main power higher than or equal to the reference level.

The harvester 320 generates (harvests) power from a signal recognized from the outside of the biosignal processing apparatus 10 (specifically, an integrated circuit for processing biosignals). The harvester 320 is configured to generate harvesting power that may be used by the digital conversion unit 100 and the AI block 500 of the integrated circuit for processing biosignals and the external biosensor 20. The harvester 320 harvests power from a solar signal, an RF signal, and/or a vibration/electrostatic signal, and outputs the harvested power to the third multiplexer 330 and the harvesting power output terminal 700 located at the rear stage (see (h) in FIG. 3). The harvesting power output terminal 700 may be connected to the capacitor 90, and the harvesting power may be stored in the capacitor 90.

The detailed structure of the harvester 320 will be described in more detail with reference to FIG. 4.

The third multiplexer 330 is connected to the harvesting power output from the harvester 320 and the main power of the main power input terminal 900, and selects and outputs the harvesting power or the main power according to the detection signal received from the main power detector 310.

The third multiplexer 330 receiving a detection signal indicating detection of the main power outputs the main power, and the third multiplexer 330 receiving a detection signal indicating non-detection of the main power selects and outputs the harvesting power. The harvesting power input into the third multiplexer 330 may be power currently being harvested (produced) by the harvester 320 or the power stored through the capacitor 90.

One or more low dropouts (LDOs) 340 generate DC power of a specified level from input power. One LDO 340 supplies DC power of a specified level to the demultiplexer 110, the trans-impedance amplifier 120, the low-noise amplifier 130, the first multiplexer 140, and the like, and another LDO 350 supplies DC power of a specified level to the temperature sensor 160, the PGA 150, the second multiplexer 170, the ADC 180, the AI block 500, and the like. Still another LDO 360 outputs biopower to the biosensor 20 outside the integrated circuit for processing biosignals through the biopower output terminal 700.

In this way, the power output from the third multiplexer 330 through the LDOs 340, 350, and 360 is supplied to the digital conversion unit 100, the AI block 500, and the external biosensor 20.

The AI block 500 includes an analog Process-In-Memory (PIM) 550 therein, and processes a plurality of biodata converted through the internal digital conversion unit 100 according to an artificial intelligence processing flow using the analog PIM 550, and outputs a result data according to processing of the plurality of biodata.

The AI block 500 may receive and store an array of N*N biodata (N is greater than or equal to 2, for example, N is 8, 16, 32, or the like) in the Memory 530 through the digital conversion unit 100, and output a result data processed (predicted) by applying an artificial intelligence algorithm to the stored biodata array to the result data output terminal 700.

For example, the AI block 500 predicts infection of a disease learned from the biodata and outputs a predicted result to the result data output terminal 700. Alternatively, the AI block 500 may predict an output signal to be transmitted to a broken neural network of a human body from a biodata corresponding to a biosignal (neural signal) received from a nerve cell of the human body, and output the predicted signal to the RF module 80 through the result data output terminal 700. The AI block 500 may transmit the predicted signal to the neural signal receiving module through the RF module 80.

The AI block 500 will be described in more detail with reference to FIGS. 5 to 7.

As shown in FIG. 3, the biosignal processing apparatus 10 including the AI block 500, the digital conversion unit 100, and the power supply unit 300 may be implemented as an integrated circuit for processing biosignals including an input terminal 900 and an output terminal 700. Since the biosignal processing apparatus 10 implemented as an integrated circuit may be miniaturized while consuming low power, it may be embedded in or attached to a human body in addition to a diagnostic kit, and may operate by harvesting power from an external signal without supply of external power.

Figure 4:
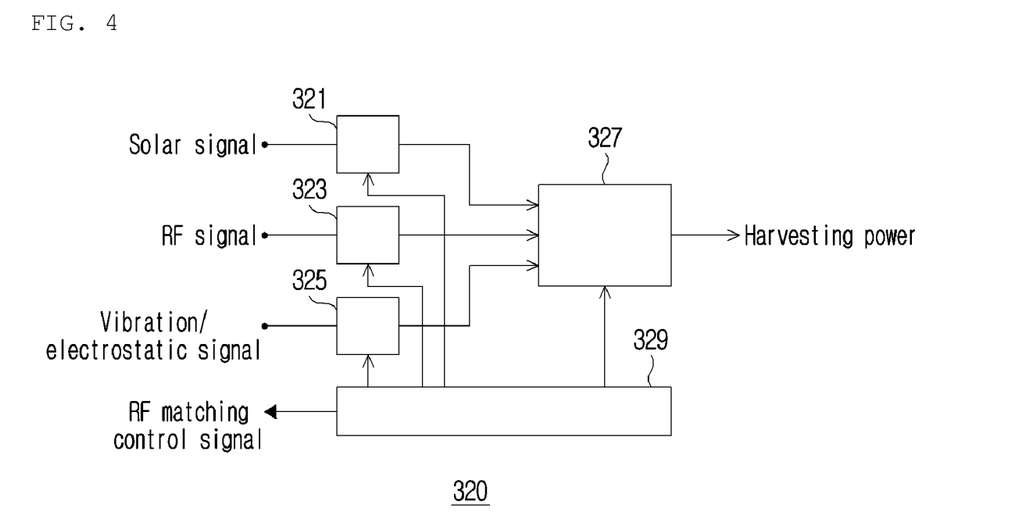
FIG. 4 is a detailed block diagram showing an example of a harvester.

FIG. 4 is a detailed block diagram showing an example of a harvester 320.

According to FIG. 4, the harvester 320 that generates harvesting power from a signal existing outside the integrated circuit for processing biosignals is configured to include a solar energy harvester 321, an RF harvester 323, a vibration/electrostatic harvester 325, a buck-boost converter 327, and a harvester controller 329. The integrated circuit for processing biosignals including the harvester 320 is attached to, embedded in, or included in a human body, generates harvesting power from a signal existing outside the human body, and operates without main power supplied from the outside, to perform a specified function (e.g., medical functions such as transmitting predicted neural network signals).

The solar energy harvester 321 harvests power from a solar signal output from the solar input terminal 900. The solar energy harvester 321 includes a voltage booster and a Maximum Power Point Tracker (MPPT) to output optimized power by dynamically adapting to changes in the solar signal. The solar energy harvester 321 may output power amplified from micro power received from the solar cell 30 to a specified level.

The RF harvester 323 harvests (generates) power from an RF signal output from the RF input terminal 900. The RF harvester 323 includes a reconfigurable RF-DC converter therein to generate and output DC power from the RF signal output from the RF input terminal 900. The RF harvester 323 including the reconfigurable RF-DC converter may tune the RF-DC converter (e.g., adjust an internal core switch, etc.) according to a control signal received from the harvester controller 329.

The vibration/electrostatic harvester 325 harvests (generates) power from a vibration/electrostatic signal output from the vibration/static-electricity input terminal 900. The vibration/electrostatic harvester 325 including a rectifier (e.g., a full bridge rectifier or a half bridge rectifier) may generate DC power from a vibration/electrostatic signal input through the limiter 50.

The buck-boost converter 327 increases (boosting mode) or decreases (buck mode) the DC power received from one or more among the solar energy harvester 321, the RF harvester 323, and/or the vibration/electrostatic harvester 325, and outputs the increased or decreased DC power. The buck-boost converter 327 may output the increased or decreased DC power (harvesting power) to the third multiplexer 330. The harvesting power output through the buck-boost converter 327 may also be stored through the capacitor 90 outside the integrated circuit for processing biosignals.

The buck-boost converter 327 may further include switches (or relays) for connecting or disconnecting the DC power of the solar energy harvester 321, the RF harvester 323, and/or the vibration/electrostatic harvester 325 to or from an internal buck-boost converting module.

The harvester controller 329 controls generation of harvesting power. The harvester controller 329 controls the solar energy harvester 321, the RF harvester 323, and/or the vibration/electrostatic harvester 325 to generate harvesting power from a signal existing outside (e.g., outside a human body).

For example, the harvester controller 329 may control the MPPT of the solar energy harvester 321 to generate optimized DC power from the solar signal.

Alternatively, the harvester controller 329 may control the RF matching network 40 and the RF harvester 323 to generate DC power from an arbitrary RF signal existing outside.

For example, the harvester controller 329 outputs a control signal for matching the RF matching network 40 to the 2.4 GHz ISM band to the RF matching network 40 through the matching network control output terminal 700. The RF matching network 40 is matched to the 2.4 GHz ISM band (e.g., a circuit is changed for impedance matching), and the RF harvester 323 receives an RF signal from the RF matching network 40 through the RF input terminal 900, and generates and outputs RF DC power from the RF signal. The harvester controller 329 measures RF DC power corresponding to the 2.4 GHz ISM band. For example, the harvester controller 329 may measure the signal strength of the RF DC power and/or the magnitude of the DC power.

Thereafter, the harvester controller 329 outputs a control signal for matching the RF matching network 40 to the 5.8 GHz ISM band to the RF matching network 40 through the matching network control output terminal 700. The RF matching network 40 is matched to the 5.8 GHz ISM band (e.g., a circuit is changed for impedance matching), and the RF harvester 323 receives an RF signal from the RF matching network 40 through the RF input terminal 900, and generates and outputs RF DC power from the RF signal. The harvester controller 329 measures RF DC power corresponding to the 5.8 GHz ISM band. For example, the harvester controller 329 may measure the signal strength of the RF DC power and/or the magnitude of the DC power.

The harvester controller 329 outputs a control signal for matching to a specific ISM band to the RF matching network 40 through the matching network control output terminal 700, and reconfigures the RF harvester 323 based on the DC power measurement signal of the 2.4 GHz ISM band and the measurement signal of the 5.8 GHz ISM band.

For example, the harvester controller 329 compares the DC power measurement signal of the 2.4 GHz ISM band with the measurement signal of the 5.8 GHz ISM band, and outputs a control signal for matching to a specific ISM band having a higher measurement signal through the matching network control output terminal 700. In addition, the harvester controller 329 reconfigures the RF harvester 323 by outputting a control signal for tuning in order to increase power generation efficiency of the RF-DC converter to the RF harvester 323.

As the integrated circuit for processing biosignals is embedded in or attached to a human body by the harvester 320 as shown in FIG. 4, power may be supplied to internal blocks using a signal existing outside a human body without supplying power from the outside. Accordingly, the integrated circuit for processing biosignals may be used as a medical device for neural network signal transfer or the like.

Figure 5:
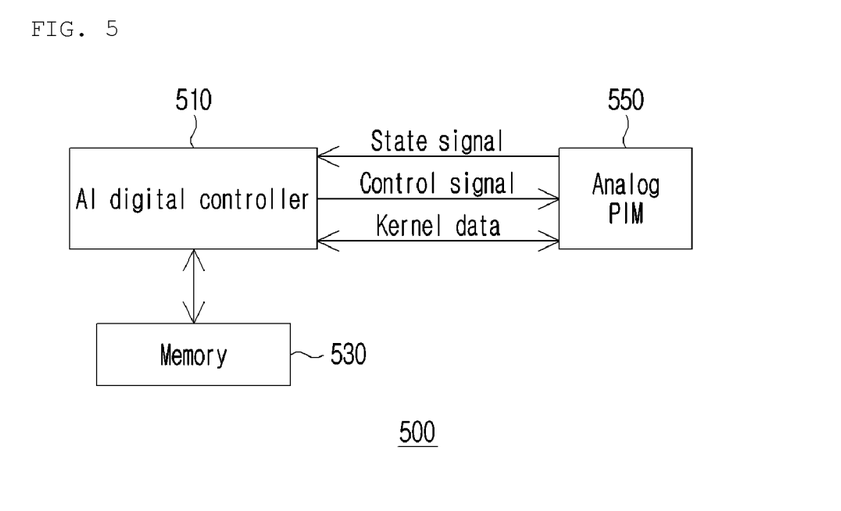
FIG. 5 is a detailed block diagram showing an example of an AI block.

FIG. 5 is a detailed block diagram showing an example of an AI block 500.

According to FIG. 5, the AI block 500 includes an AI digital controller 510, a Memory 530, and an analog PIM 550.

Describing the detailed blocks of the AI block 500 shown in FIG. 5, the Memory 530 includes volatile memory and/or non-volatile memory and stores various data. The Memory 530 may store at least a plurality of biodata converted by the digital conversion unit 100 and various data generated by artificial intelligence processing on the plurality of biodata.

For example, the Memory 530 may receive and temporarily store a plurality of digital biodata (e.g., an array of N*N biodata, N is an integer such as 8, 16, 32, or the like) converted by one or more ADCs 180 of the digital conversion unit 100 under the control of the AI digital controller 510.

The analog PIM 550 includes an SRAM array 554 to store a plurality of analog data of each of a plurality of kernel data used for convolution operation. The analog PIM 550 may update analog data of a plurality of kernels (or 'filters') of the SRAM array 554 under the control of the AI digital controller 510, and output digital data corresponding to the analog data.

The analog PIM 550 may perform a specified function according to a control signal received from the AI digital controller 510, and output a state signal according to execution of the function to the AI digital controller 510. In addition, the analog PIM 550 may receive one or a plurality of digital kernel data (to be updated) from the AI digital controller 510, convert the digital kernel data into analog data, and store the analog data in the internal SRAM 554-1. In addition, the analog PIM 550 may convert the analog kernel data stored into digital kernel data and output the digital kernel data to the AI digital controller 510.

The area and power consumption required for storing the kernel data may be minimized by the analog PIM 550 that can store and update analog kernel data.

Figure 6:
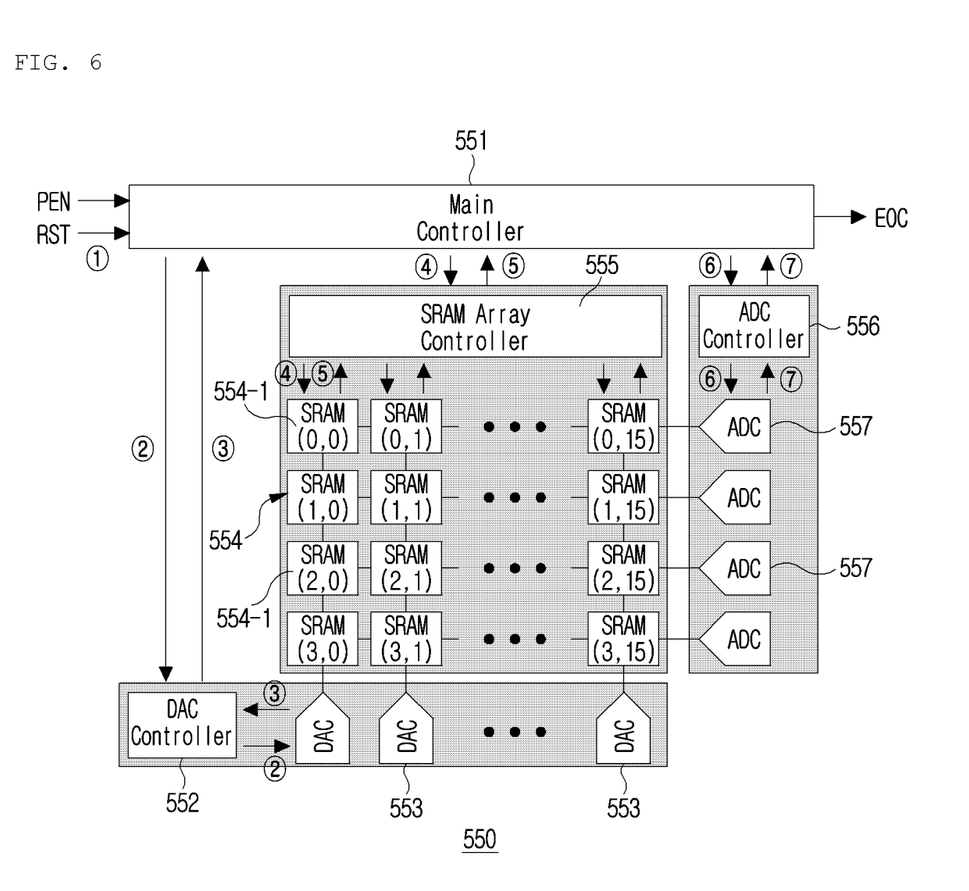
FIG. 6 is a view showing a detailed configuration of an example of an analog PIM.

FIG. 6 is a view showing a detailed configuration of an example of an analog PIM 550.

According to FIG. 6, the analog PIM 550 is configured to include a main controller 551, a DAC controller 552, a plurality of DACs 553, an SRAM array 554, an SRAM array controller 555, an ADC controller 556, and a plurality of ADCs 557.

The main controller 551 controls the overall operation inside the analog PIM 550. The main controller 551 initializes the SRAM array 554 according to a control signal (see ①in FIG. 6) received from the AI digital controller 510, controls the DAC controller 552 to convert digital kernel data into analog data, controls the SRAM array controller 555 to store the converted analog data in the SRAM 554-1, or controls the ADC controller 556 to convert the analog data of the SRAM 554-1 into digital data, and output the digital data to the AI digital controller 510.

The DAC 553 converts a digital data of multiple bits into an analog data (signal) of a single signal. The DAC 553 converts an input kernel data of 8 bits, 12 bits, or 16 bits into an analog signal and outputs the analog signal under the control of the DAC controller 552. The analog PIM 550 has a plurality of DACs 553, for example, as many DACs 553 as the size of the kernel array of a single kernel (channel) (e.g., 4*4 matrix (16 DACs), 3*3 matrix (9 DACs)).

Each DAC 553 may convert each kernel data of the kernel array input from the AI digital controller 510 into an analog data (analog signal) under the control by the DAC controller 552.

The DAC controller 552 controls generation of analog data corresponding to kernel data by controlling a plurality of connected DACs 553 according to a control signal (see ② in FIG. 6) received from the main controller 551. For example, the DAC controller 552 may generate an analog power signal proportional to the bit value of the kernel data in the DAC 553 by turning on the transistor of the DAC 553 for a time period corresponding to the bit value of the kernel data of the kernel array input into each DAC 553.

The DAC controller 552 converts all kernel data of each of all the connected DACs 553 into analog signals according to the bit value, and when conversion of all the kernel data into analog data is completed, a state signal indicating completion of conversion is output to the main controller 551 (see ③ in FIG. 6).

The SRAM array 554 stores analog data corresponding to the kernel data of the kernel array (matrix). The SRAM array 554 stores analog data of the kernel array of a plurality of kernels (channels). For example, the SRAM array 554 may store analog data (signals) of a 4*4 or 3*3 kernel array (matrix) of 4 channels (or 3 channels).

The SRAM array 554 has 16 or 9 SRAMs 554-1 for each kernel (channel) according to the size of the kernel array, and the plurality of SRAMs 554-1 of each kernel is connected to a corresponding DAC 553. The SRAM array 554 includes a plurality of SRAMs 554-1 for each kernel as many as the number of kernels (e.g., SRAMs 554-1 as many as 4*16 when the number of kernels is 4 and the kernel size is 16).

Each SRAM 554-1 of the SRAM array 554 stores analog data (signal) received from the connected DAC 553 under the control of the SRAM array controller 555. The SRAM 554-1 includes 6, 8 or 10 transistors to store the analog data (analog signal), and may change (update) the stored analog data according to a control signal received from the SRAM array controller 555.

The SRAM array controller 555 controls the SRAM array 554. The SRAM array controller 555 stores analog data received from the connected DAC 553 in a plurality of SRAMs 554-1 of a specific kernel among a plurality of kernels of the SRAM array 554 under the control of the main controller 551 (see ④ in FIG. 6), and outputs a storage completion state to the main controller 551 (see ⑤ in FIG. 6).

The ADC 557 converts analog data (signal) into digital data of multiple bits. The ADC 557 is connected to the SRAM 554-1 of the SRAM array 554 to convert the analog data of the SRAM 554-1 into digital data of a specified number of bits (e.g., 8, 12, 16, or the like).

The analog PIM 550 has a plurality of ADCs 557, and for example, ADCs 557 as many as the number of multiple kernels (channels) (e.g., 4, 3, or the like) or as many as a multiple of the number of multiple kernels (channels) (e.g., 16, 12, or the like).

The ADC controller 556 controls conversion of the analog data of the SRAM 554-1 into digital data of a specified number of bits by controlling a plurality of connected ADCs 557 according to a control signal (⑥ in FIG. 6) received from the main controller 551. For example, the ADC controller 556 includes one or more comparators (e.g., as many as the number of ADCs 557 of the analog PIM 550) for comparing the voltage signal output according to turn-on of the transistor of each ADC 557 with the analog data (signal) of the connected SRAM 554-1 after the control begins, and may output a value of time (clock counting value) until when the two signals match as a digital data.

When digital data conversion is completed for all ADCs 557, the ADC controller 556 may output a state signal indicating completion of data conversion to the main controller 551 (see ⑦ in FIG. 6). As the state signal is received, the main controller 551 may output a state signal to the AI digital controller 510.

Describing again the configuration of the AI block 500 of FIG. 5, the AI digital controller 510 generates a result data predicted for the biosignal of the biosensor 20 output from the biosignal input terminal 900 by applying the processing flow of an artificial intelligence algorithm using digital data corresponding to each of the kernels of the analog PIM 550 and the biodata array (a plurality of biodata) of the Memory 530, and outputs the generated result data to the result data output terminal 700.

Figure 7:
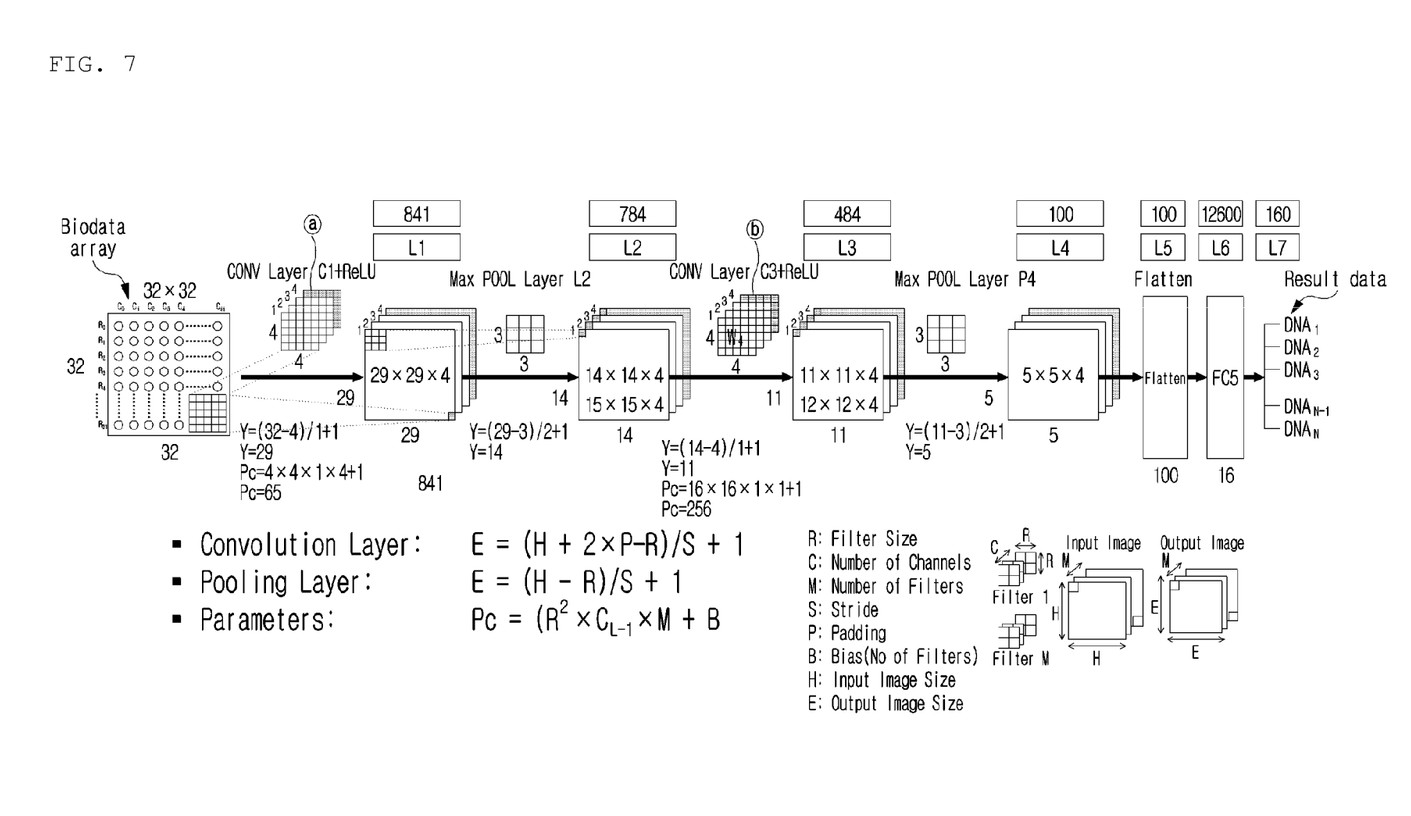
FIG. 7 is a view showing an exemplary processing flow of an artificial intelligence algorithm performed by an AI digital controller in an integrated circuit for processing biosignals.

FIG. 7 is a view showing an exemplary processing flow of an artificial intelligence algorithm performed by an AI digital controller 510 in an integrated circuit for processing biosignals. The example of FIG. 7 shows an example of a processing flow applying a Convolutional Neural Network (CNN) algorithm.

Describing an example of applying the CNN algorithm in connection with the integrated circuit for processing biosignals, first, the AI digital controller 510 configures a biodata array (matrix). The AI digital controller 510 may control supply of biopower to the biosensor 20, and may receive N*N (e.g., 32*32) biodata through the digital conversion unit 100 and temporarily store the biodata in the Memory 530.

In addition, the AI digital controller 510 may store data of the kernel array of a plurality of kernels for a first convolution operation in the analog PIM 550. The AI digital controller 510 may store the kernel array digital data of a plurality of kernels for the first (initial) convolution operation configured according to prior artificial intelligence learning in the non-volatile Memory 530 or the like in advance, and the AI digital controller 510 may convert digital data of a plurality of kernels into analog data under the control of the main controller 551 of the analog PIM 550 at the time of driving or when the artificial intelligence initially begins processing, and store the converted analog data in the analog PIM 550. Alternatively, the AI digital controller 510 may directly store, in the analog PIM 550 in advance, analog data corresponding to the digital data of the kernel array of a plurality of kernels for the first (initial) convolution operation configured according to prior artificial intelligence learning.

In the first convolution operation process, the AI digital controller 510 that performs (processes) the CNN algorithm through an internally configured digital control circuit generates a plurality of feature maps by a convolution operation between a plurality of biodata of the biodata array stored in the Memory 530 and corresponding digital data of a plurality of kernels of the analog PIM 550, and stores the generated feature maps in the Memory 530.

The AI digital controller 510 may control the analog PIM 550 to load the digital data of the kernel array of a plurality of kernels (see ⓐ in FIG. 7) on the Memory 530, and generate and store a feature map for each kernel through a convolution operation with the biodata. Thereafter, the AI digital controller 510 applies an ReLU operation, which is an activation function, to the feature map and applies a max pool operation.

In addition, the AI digital controller 510 updates the digital data of the kernel array of a plurality of kernels according to application of the first convolution operation and the ReLU and max pool operations. The AI digital controller 510 controls the main controller 551 of the analog PIM 550 according to update of the kernel array according to the CNN algorithm to store digital data of each of a plurality of kernels, which will be used in the subsequent convolution operation process, in the SRAM array 554 of the analog PIM 550.

Thereafter, the AI digital controller 510 performs convolution operation, ReLU operation, and max pool operation on the updated kernel array of the plurality of kernels (see ⓑ in FIG. 7) and the feature map generated according to the max pool processing in the first convolution operation process.

The AI digital controller 510 performs the convolution, ReLU, and max pool operations multiple times that is set according to the characteristic of a prediction target, generates a prediction result data through a flattening process or the like, and outputs the generated result data through the data output terminal 700.

The AI digital controller 510 configured according to the present invention may be configured to perform a fixed iterative operation layer (convolution, ReLU, and max pool) in advance or variably perform an iterative operation layer according to the characteristic of a prediction target.

The AI digital controller 510 that processes the CNN algorithm or the like may predict infection of a disease from biodata and output a predicted result data, or predict an output signal of the neural network of a human body from the biodata of nerve cells and output the predicted signal as a result data.

The biosignal processing apparatus 10 including the AI digital controller 510, the Memory 530, the analog PIM 550 and the like is configured as an integrated circuit to reduce the size, weight, and power consumption. In addition, as the AI block 500 (AI engine) is mounted on the integrated circuit, accurate prediction is possible from biodata, and accuracy of prediction can be improved repeatedly.

As the present invention described above may be substituted, modified, and changed in various ways by those skilled in the art without departing from the technical spirit of the present invention, the present invention is not limited by the above embodiments and the accompanying drawings.

The integrated circuit for processing biosignals, the biosignal processing apparatus, and the biosignal processing system have an effect capable of detecting diseases from biosignals received from a human body or connecting damaged nerves, and reducing the size and power consumption, while being able to be mass produced.

The integrated circuit for processing biosignals, the biosignal processing apparatus, and the biosignal processing system have an effect capable of improving and reducing a false detection rate of disease by utilizing an artificial intelligence engine that can be widely and generally used, learned, and updated by interfacing with various types of biosensors.

The integrated circuit for processing biosignals, the biosignal processing apparatus, and the biosignal processing system have an effect capable of harvesting power needed inside the integrated circuit from various types of external signals, and providing the power to the integrated circuit that processes the biosignals, while being able to be used in various biosignal processing environments.

The effects that can be obtained from the present invention are not limited to the effects mentioned above, and unmentioned other effects will be clearly understood by those skilled in the art from the descriptions described above.

What is claimed is:

1. An integrated circuit for processing biosignals, the integrated circuit comprising:
   a digital conversion unit for converting an analog biosignal input through a biosignal input terminal into a digital biodatas; and
   an Artificial Intelligence (AI) block for processing a plurality of biodatas converted through the digital conversion unit according to an artificial intelligence processing flow, and outputting result data according to processing of the plurality of biodatas,
   wherein the digital conversion unit includes:
   a demultiplexer for outputting an analog biosignal output from the biosignal input terminal to a first output line or a second output line according to a type signal that is input through a type input terminal;
   a trans-impedance amplifier for amplifying the analog biosignal of the first output line and outputting the amplified biosignal;
   a low-noise amplifier for amplifying the analog biosignal of the second output line and outputting the amplified biosignal; and
   a first multiplexer for outputting a biosignal selected from the biosignal of the trans-impedance amplifier and the biosignal of the low-noise amplifier according to the type signal.

2. The integrated circuit according to claim 1, wherein the digital conversion unit further includes: a temperature sensor;
   a second multiplexer for outputting the biosignal output from the first multiplexer or a temperature signal output from the temperature sensor according to a selection signal received from the AI block; and
   an Analog to Digital Converter (ADC) for converting an analog signal output from the second multiplexer into digital data.

3. The integrated circuit according to claim 2, wherein the digital conversion unit includes the demultiplexer, the trans-impedance amplifier, the low-noise amplifier, the first multiplexer, the second multiplexer, and the ADC in plurality to independently convert analog biosignals input through a plurality of biosignal input terminals into a plurality of digital biodatas, and output the digital biodatas to the AI block.

4. The integrated circuit according to claim 1, further comprising a power supply unit for supplying power to the digital conversion unit and the AI block from a supplied main power or a signal recognized from the outside, wherein the power supply unit outputs power generated from the signal recognized from the outside to the digital conversion unit and the AI block as a voltage of a specified level according to whether the main power is detected.

5. The integrated circuit according to claim 4, wherein the power supply unit includes: a main power detector for detecting the main power from a main power input terminal, and outputting a detection signal indicating whether or not the main power is detected;
   a harvester for generating power from a signal recognized from the outside of the integrated circuit for processing biosignals; and
   a third multiplexer for selecting and outputting one among the power from the harvester and the main power of the main power input terminal according to the detection signal of the main power detector, wherein the power output from the third multiplexer is supplied to the digital conversion unit and the AI block.

6. The integrated circuit according to claim 5, wherein the harvester includes:
   a solar energy harvester for harvesting power from a solar signal output from a solar input terminal;
   a radio frequency (RF) harvester for harvesting power from an RF signal output from an RF input terminal;
   a vibration/electrostatic harvester for harvesting power from a vibration/electrostatic signal output from a vibration/static-electricity input terminal; and
   a buck-boost converter for increasing or decreasing power received from one or more among the solar energy harvester, the RF harvester, and the vibration/electrostatic harvester, and outputting the increased or decreased power to the third multiplexer.

7. The integrated circuit according to claim 6, wherein the solar energy harvester includes a Maximum Power Point Tracker (MPPT), the RF harvester includes a reconfigurable RF-DC converter, and the vibration/electrostatic harvester includes a rectifier, wherein the harvesting power output through the buck-boost converter is stored through a capacitor outside the integrated circuit for processing biosignals.

8. The integrated circuit according to claim 1, wherein the AI block predicts infection of a disease from the biodatas and outputs a predicted result, or predicts an output signal of a neural network of a human body from the biodatas and outputs the predicted signal.

9. A biosignal processing apparatus comprising:
   a digital conversion unit for converting an analog biosignal into a digital biodatas; and
   an Artificial Intelligence (AI) block for processing a plurality of biodatas converted through the digital conversion unit according to an artificial intelligence processing flow and outputting result data according to processing of the plurality of biodatas using an analog Processing in Memory (PIM),
   wherein the AI block includes:
   a memory for storing a plurality of biodatas received from the digital conversion unit;
   the analog PIM capable of storing a plurality of analog data of each of a plurality of kernels, updating the plurality of analog data of the plurality of kernels, and outputting a plurality of digital data corresponding to the plurality of kernels; and
   an AI digital controller for generating predicted result data by applying a processing flow of an artificial intelligence algorithm using a plurality of corresponding digital data of the plurality of kernels received from the analog PIM, and the plurality of biodatas of the memory,
   wherein the AI digital controller applying a Convolutional Neural Network (CNN) algorithm generates a plurality of feature maps by a convolution operation between the plurality of biodatas of the memory and the plurality of corresponding digital data of the plurality of kernels of the analog PIM, and stores the feature maps in the memory in a first convolution operation process, and generates a plurality of digital data of a plurality of kernels to be used in a second convolution operation process subsequent to the first convolution operation process, and stores a plurality of digital data of each of a plurality of kernels to be updated in the analog PIM.

10. The apparatus according to claim 9, wherein the analog PIM includes:
    M Digital to Analog Converters (DACs);
    a Static Random Access Memory (SRAM) array including L of M SRAMs respectively connected the M DACs according to the number of the plurality of kernels, each SRAM storing analog data received from a connected DAC; and
    L or more Analog to Digital Converters (ADCs) connected to the SRAMs of the SRAM array to convert an analog data of the SRAM into digital data of a specified number of bits, wherein M and L are equal to or greater than 2.

11. The apparatus according to claim 9, wherein the biosignal processing apparatus is an integrated circuit for processing biosignals.

12. A biosignal processing system comprising the integrated circuit for processing biosignals of claim 1.

13. The system according to claim 12, further comprising:
    a capacitor for storing harvesting power; and
    a biosensor for generating an analog biosignal using power harvested by the integrated circuit for processing biosignals, and outputting the generated analog biosignal of current or voltage to a biosignal input terminal of the integrated circuit for processing biosignals, wherein the integrated circuit for processing biosignals including a digital conversion unit and an AI block further includes a harvester for generating harvesting power that can be used by the biosensor.

14. The system according to claim 13, further comprising:
    a Radio Frequency (RF) matching network capable of matching an RF signal of a first Industrial Scientific Medical (ISM) band or a second ISM band; and
    a limiter for limiting a vibration/electrostatic signal according to vibration/static electricity,
    wherein the harvester of the integrated circuit for processing biosignals includes:
    an RF harvester for harvesting power from the RF signal output from an RF input terminal;
    a vibration/electrostatic harvester for harvesting power from the vibration/electrostatic signal output from a vibration/static-electricity input terminal;
    a buck-boost converter for increasing or decreasing power received from one or more among the RF harvester and the vibration/electrostatic harvester, and outputting the increased or decreased power as harvesting power; and a harvester controller for controlling generation of harvesting power from an external signal by controlling the RF harvester and the vibration/electrostatic harvester.

15. The system according to claim 14, wherein the harvester controller outputs a control signal for matching to the first ISM band to the RF matching network through an output terminal, measures a first RF power generated by the RF harvester, and then outputs a control signal for matching to the second ISM band to the RF matching network through the output terminal, measures a second RF power generated by the RF harvester, and then outputs a control signal for controlling the RF matching network based on a measurement signal of the first RF power and a measurement signal of the second RF power, and reconfigures the RF harvester.

16. The system according to claim 12, further comprising an RF module for transmitting a radio signal, wherein an AI block of the integrated circuit for processing biosignals predicts a signal output through a neural network of a human body from a biosignal received from a nerve cell of the human body, and transmits a data indicating the predicted signal through the RF module.

17. The system according to claim 12, wherein the biosignal processing system is a diagnostic kit that predicts infection of a disease from blood or body fluid or a medical device that can replace a signal of a neural network of a human body, using a learned artificial intelligence technique.

* * * * *